US00PP33432P3

(12) United States Plant Patent
van der Knaap

(10) Patent No.: US PP33,432 P3
(45) Date of Patent: Aug. 31, 2021

(54) ***DIEFFENBACHIA* PLANT NAMED 'MAROBA 3'**

(50) Latin Name: ***Dieffenbachia* Schott.**
Varietal Denomination: MAROBA 3

(71) Applicant: Eduard J. M. van der Knaap, Bleiswijk (NL)

(72) Inventor: Eduard J. M. van der Knaap, Bleiswijk (NL)

( * ) Notice: Subject to any disclaimer, the term of this patent is extended or adjusted under 35 U.S.C. 154(b) by 0 days.

(21) Appl. No.: 17/104,575

(22) Filed: Nov. 25, 2020

(65) Prior Publication Data

US 2021/0168985 P1 Jun. 3, 2021

(30) Foreign Application Priority Data

Nov. 29, 2019 (QZ) ..... PBR 2019/3233

(51) Int. Cl.
*A01H 5/12* (2018.01)
*A01H 6/12* (2018.01)
*A01H 6/10* (2018.01)

(52) U.S. Cl.
USPC ..... Plt./378
CPC ..... *A01H 6/12* (2018.05); *A01H 6/10* (2018.05)

(58) Field of Classification Search
USPC ..... Plt./378
CPC ..... A01H 6/10
See application file for complete search history.

*Primary Examiner* — Anne Marie Grunberg
(74) *Attorney, Agent, or Firm* — Samuel R. McCoy, Jr.

(57) ABSTRACT

'MAROBA 3' is a new and distinctive variety of *Dieffenbachia* plant which is characterized by a compact, upright growth habit with an abundance of dark green, glossy foliage borne on dark green petioles, unique foliage variegation with a moderate amount light greyed-green blotches along the secondary leaf veins with sparse blotches following a similar pattern in the interveinal areas, and the stability of all characteristics from generation to generation.

2 Drawing Sheets

Latin name of the genus and species: The Latin name of the genus and species of the novel variety disclosed herein is *Dieffenbachia* Schott.

Variety denomination: The inventive variety of *Dieffenbachia* disclosed herein has been given the variety denomination 'MAROBA 3'.

CROSS REFERENCE TO RELATED APPLICATIONS

This application claims priority to the Community Plant Variety Rights application number 2019/3233, filed Nov. 29, 2019, which is herein incorporated by reference.

BACKGROUND OF THE INVENTION

Parentage: 'MAROBA 3' originated as a naturally-occurring, whole plant mutation of *Dieffenbachia* 'MAROBA' (U.S. Plant Pat. No. 9,220). In August of 2018 the inventor discovered the mutation at a commercial greenhouse in Bleiswijk, the Netherlands, growing amongst a crop of *Dieffenbachia* 'MAROBA'. The mutation was noted for its freely-branching, compact growth habit, and unique foliage variegation and was subsequently isolated for further evaluation in order to confirm the distinctness and stability of the characteristics first observed. Upon confirmation of distinctness and stability, the new *Dieffenbachia* plant was selected for commercialization and given the name 'MAROBA 3'.

Asexual Reproduction: Asexual reproduction of 'MAROBA 3', by way of softwood stem cuttings, was first performed in the November of 2020 at a commercial greenhouse in Bleiswijk, the Netherlands. Five successive generations so produced have shown that the unique features of the instant cultivar are stable and reproduced true to type.

SUMMARY OF THE INVENTION

The cultivar 'MAROBA 3' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Dieffenbachia* cultivar 'MAROBA 3'. These traits, in combination, distinguish 'MAROBA 3' as a new and distinct cultivar.

1. *Dieffenbachia* 'MAROBA 3' exhibits a compact, upright growth habit with an abundance of foliage; and
2. *Dieffenbachia* 'MAROBA 3' exhibits an abundance of dark green, glossy foliage borne on dark green petioles; and
3. *Dieffenbachia* 'MAROBA 3' exhibits a unique foliage variegation pattern consisting of a moderate amount of irregular light greyed-green blotches that generally follow the secondary leaf veins with sparse blotches following a similar pattern in the interveinal areas.

Generally appearing as a darker shade of green, relative to 'REEVA'; moderately blotched with a mixture of yellow-green and greyed-green along the secondary veins which generally appears nearer to a light a very light greyed-green coloration; interveinal areas are slightly blotched yellow-green.

BOTANICAL DESCRIPTION OF THE PLANT

Figure 1:
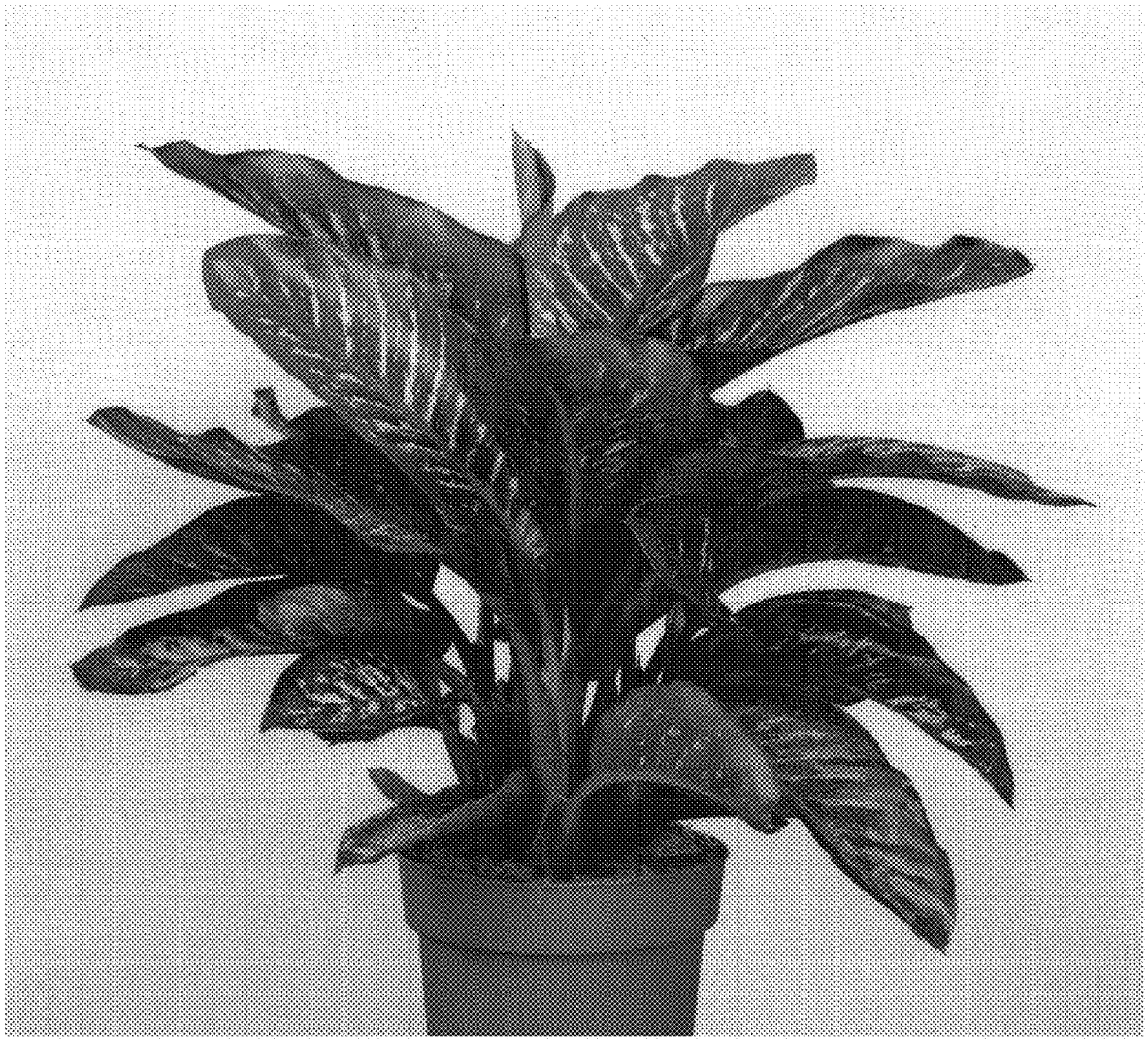
FIG. 1 shows, as nearly true as it is reasonably possible to make the same in color illustrations of this type, an exemplary 'MAROBA 3' plant at approximately 35 weeks old, potted into a 21 cm nursery container, grown in a greenhouse in Bleiswijk, Netherlands.
Figure 2:
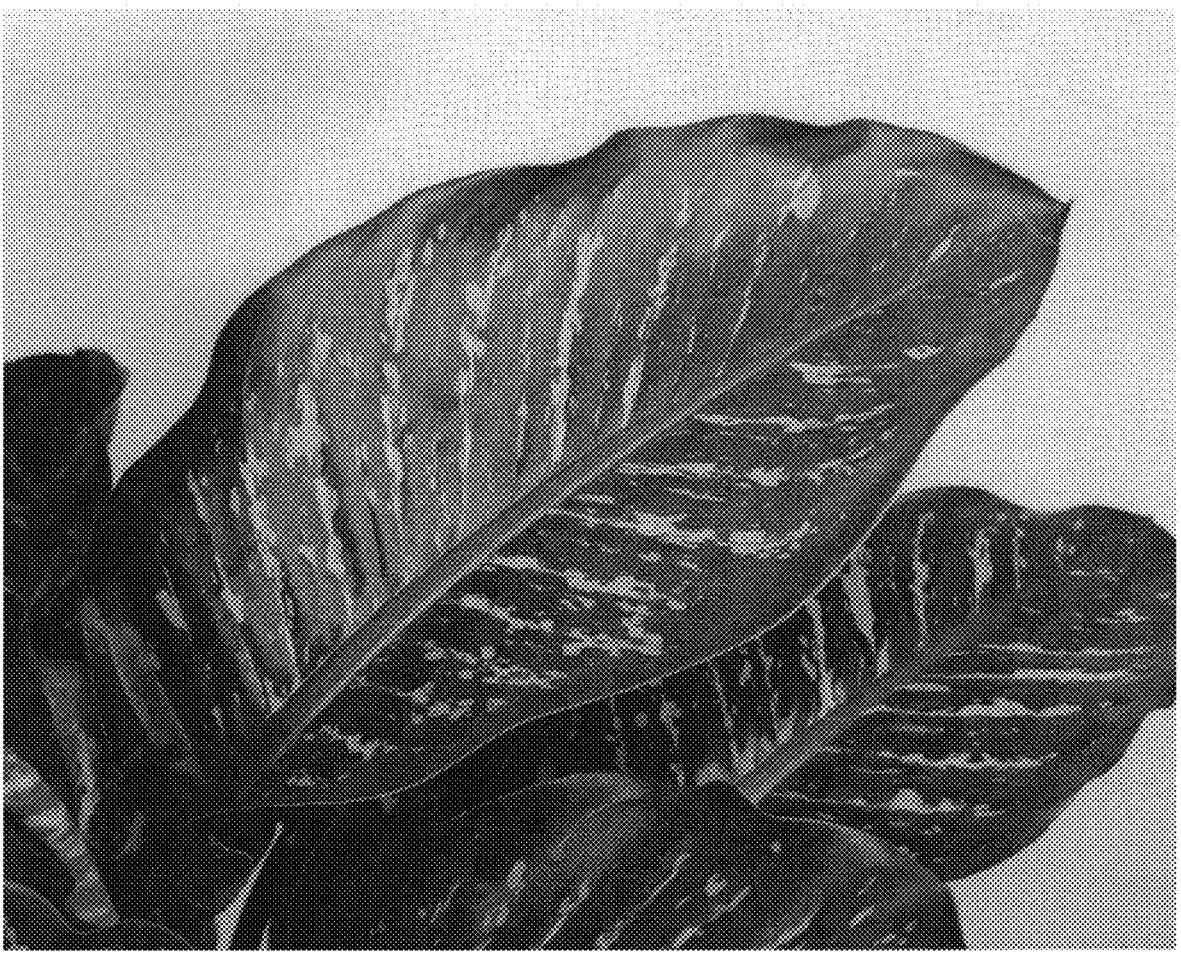
FIG. 2 shows, as nearly true as it is reasonably possible to make the same in color illustrations of this type, the typical foliage of 'MAROBA 3'.

The following is a detailed botanical description of a new and distinct variety of *Dieffenbachia* known as 'MAROBA 3', based upon observations of plants, approximately 35 weeks old from a rooted cutting, grown in 12 cm nursery container in a climate-controlled greenhouse in Bleiswijk, the Netherlands. Observation data was recorded in November of 2020. Plants were produced using conventional greenhouse production protocols for *Dieffenbachia* which consisted of regular 2.2 to 3.0 EC fertilizer applications and regular irrigation. No pest or disease control measures were utilized in production. Plants were produced under shade and no photoperiodic treatments or artificial light was given to the plants.

Those skilled in the art will appreciate that certain characteristics will vary with older or, conversely, with younger plants. 'MAROBA 3' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 edition.

A botanical description of 'MAROBA 3' and comparisons with the parent and the most similar variety of common knowledge are provided below.

General plant description:

*Growth habit.*—Clump forming, upright perennial.
*Plant form.*—Broad ovate to near spherical.
*Growth rate.*—Moderately fast to fast growing.
*Plant vigor.*—Moderately vigorous.
*Height.*—47.7 cm.
*Width.*—61.8 cm.
*Propagation.*—Softwood stem cuttings.
*Time to initiate roots.*—Approximately 21 days to initiate roots at approximately 24 degrees Centigrade.
*Time to produce a finished plant.*—Approximately 7 weeks to produce a fully rooted cutting and 30 weeks to produce a finished plant.
*Environmental tolerances.*—USDA Zones 10 to 13; at least tolerant of temperatures of up to 40 degrees Celsius. Moderate to high tolerance to rain inundation; low tolerance to wind. Not drought tolerant.
*Pest resistance and susceptibility.*—Plants have not been observed to be susceptible or resistant to pathogens and pests common to *Dieffenbachia.*

Root system:

*General.*—Fleshy; sparsely branched, and moderately dense to dense root system.
*Diameter of primary roots.*—0.5 cm.
*Color.*—Yellow-white, nearest to a mixture of RHS 158B and 158C.
*Texture.*—Densely covered with minute root hairs.

Stems:

*Branching habit.*—Main shoots arise directly from the soil and only occasionally branch.
*Number of main shoots per plant.*—5.
*Number of lateral branches per plant.*—1.
*Appearance; cross-section.*—Rounded.
*Length of main shoots.*—14.0 cm.
*Diameter of main shoots.*—4.3 cm.
*Internode length on main shoots.*—2.4 cm.
*Aspect.*—Erect; near vertical.
*Strength.*—Strong.
*Texture and luster.*—Glabrous, smooth and moderately glossy.
*Color, juvenile.*—Yellow-green, nearest to RHS 145C.
*Color, mature.*—Yellow-green, nearest to RHS 145A.
*Color at internodes.*—Yellow-green, nearest to RHS 145A.

Foliage:

*Arrangement.*—Alternate.
*Division.*—Simple.
*Quantity of leaves per lateral branch.*—Average of 10.
*Leaf shape.*—Ovate.
*Leaf apex.*—Apiculate with an abruptly acute tip.
*Leaf base.*—Truncate.
*Aspect.*—Slightly to moderately carinate, slightly reflexed.
*Attitude.*—Upward and outward.
*Leaf length.*—Average 29.8 cm in length.
*Leaf width.*—Average 16.9 cm in width.
*Leaf margin.*—Entire; moderately undulate.
*Texture, adaxial surface.*—Glabrous, glabrous and moderately glossy.
*Texture, abaxial surface.*—Glabrous, glabrous and slightly glossy.
*Juvenile color, adaxial surface.*—Nearest to in between green and yellow-green, RHS 137B and 146A; areas surrounding the secondary veins are heavily blotched and suffused yellow-green, nearest to a combination of RHS 145C, 145D, and 150D; interveinal areas are slightly blotched yellow-green, nearest to RHS 147D.
*Juvenile color, abaxial surface.*—Nearest to yellow-green, RHS 147B; areas surrounding the secondary veins are heavily blotched and suffused with a mixture of yellow-green and greyed-green, nearest to RHS 144B, 150D, and 192A; interveinal areas are slightly blotched yellow-green, nearest to RHS 144B.
*Mature color, adaxial surface.*—Nearest to in between green and yellow-green, RHS NN137B and 147A; areas surrounding the secondary veins are moderately blotched with a mixture of yellow-green and greyed-green, nearest to RHS 148C, 148D, and 194B; interveinal areas are very slightly blotched with a mixture of yellow-green and greyed-green, nearest to RHS 148C, 194A, and 194B.
*Mature color, abaxial surface.*—Green, nearest to RHS 137B; areas surrounding the secondary veins are moderately blotched with a mixture of yellow-green and greyed-green, nearest to RHS 148D and 193A; interveinal areas are very slightly blotched with a mixture of yellow-green and greyed-green, nearest to RHS 148D and 193A.
*Venation.*—Vein pattern — Pinnate. Vein color, adaxial surface — Green, nearest to RHS 137A. Vein color, abaxial surface — Nearest to a mixture of green and yellow-green, RHS 143A and 144B.
*Petiole.*—Length — Approximately 2.3 cm, excluding the petiole wing. Diameter — Petioles are subterete with a somewhat flattened adaxial surface; average width is 1.05 cm; average height is 1.2 cm. Texture and luster, adaxial surface — Glabrous, smooth, and glossy. Texture and luster, abaxial surface — Glabrous, smooth and slightly glossy. Color, adaxial surface — Green, nearest to RHS NN137A. Color, abaxial surface — Nearest to a mixture of green and yellow-green, RHS NN137A and 144A. Strength — Strong. Geniculum — None present. Petiole wings — Length — Approximately 13.5 cm. Width — Approximately 1.4 cm. Color, outer surface — Yellow-green, nearest to RHS 146D. Color, abaxial surface — Yellow-green, nearest to RHS 146B and fading lighter distally, nearest to RHS 145A.

Inflorescence: No flowers observed to date.
Flower bud: No flowers observed to date.
Flower: No flowers observed to date.
Reproductive organs: No flowers observed to date.
Seed and fruit: No flowers observed to date.

Comparisons With the parents

Plants of the new cultivar 'MAROBA 3' differ from its parent, *Dieffenbachia* 'MAROBA' (U.S. Plant Pat. No. 9,220), by the characteristics described in Table 1.

TABLE 1

| Characteristic | 'MAROBA 3' | 'MAROBA' |
|---|---|---|
| Foliage size | Smaller than 'MAROBA'. | Larger than MAROBA 3'. |
| General coloration of the juvenile foliage; adaxial surface. | A mixture of green and yellow-green, generally appearing as a darker shade of green, relative to 'MAROBA'; heavily blotched yellow-green which generally appears nearer to a light a very light green coloration; interveinal areas are slightly blotched yellow-green, | Yellow-green, generally appearing as a lighter shade of green; moderately blotched with a mixture of green and yellow-green which generally appears nearer to a yellow or green-yellow coloration. Irregularly, broadly margined green. |
| General coloration of the mature foliage; adaxial surface. | A mixture of green and yellow-green, generally appearing as a darker shade of green, relative to 'MAROBA'; moderately blotched with a mixture of yellow-green and greyed-green along the secondary veins which generally appears nearer to a very light greyed-green coloration; interveinal areas are slightly blotched yellow-green, | A mixture of green and yellow-green, generally appearing as a lighter shade of green; more heavily blotched with a mixture of yellow-green and greyed-green which generally appears nearer to a yellow or green-yellow coloration. Irregularly, broadly margined with a mixture of yellow-green and green. |

TABLE 1-continued

| Characteristic | 'MAROBA 3' | 'MAROBA' |
|---|---|---|
| General coloration of the main veins. | Darker shade of green, relative to 'MAROBA'. | Lighter shade of green, relative to MAROBA 3'. |

Comparisons With the Most Similar Variety of Common Knowledge

Plants of the new cultivar 'MAROBA 3' may be distinguished from the commercial variety *Dieffenbachia* 'REEVA' (U.S. Plant Pat. No. 29,666) by the combination of characteristics described in Table 2.

TABLE 2

| Characteristic | 'MAROBA 3' | 'REEVA' |
|---|---|---|
| Foliage size | Smaller than 'REEVA'. | Larger than 'MAROBA 3'. |
| General coloration of the petiole. | Darker shade of green, relative to 'REEVA'. | Lighter shade of green, relative to 'MAROBA 3'. |
| General coloration of the juvenile foliage; adaxial surface. | Generally appearing as a relative to 'REEVA'; heavily blotched yellow-green along the secondary veins, which generally appears nearer to a very light green coloration; interveinal areas are slightly blotched yellow-green. | Generally appearing as a heavily, centrally blotched with a mixture of green and yellow-green which generally appears as a light yellow-green. |
| General coloration of the mature foliage; adaxial surface. | Generally appearing as a darker shade of green, relative to 'REEVA'; moderately blotched with a mixture of yellow-green and greyed-green along the secondary veins which generally appears nearer to a very light greyed-green coloration; interveinal areas are slightly blotched yellow-green. | Generally appearing as a lighter shade of green; heavily, centrally blotched with a mixture of green and yellow-green which generally appears as a light yellow-green. |
| General coloration of the main veins. | Darker shade of green, relative to 'MAROBA'. | Lighter shade of green, relative to MAROBA 3'. |

That which is claimed is:

1. A new and distinct variety of *Dieffenbachia* plant named 'MAROBA 3', substantially as described and illustrated herein.

* * * * *